United States Patent
Luo et al.

(10) Patent No.: US 8,048,405 B2
(45) Date of Patent: Nov. 1, 2011

(54) RADIOACTIVE MIXTURE AND MANUFACTURING METHOD THEREOF

(75) Inventors: Tsai-Yueh Luo, Longtan Township, Taoyuan County (TW); I-Chung Tang, Pingjhen (TW); Show-Wen Liu, Shetou Township, Changhua County (TW); Yu-Lung Wu, Bade (TW); Cheng-Hsien Lin, Taipei (TW); Cheng-Fang Hsu, Toufen Township, Miaoli County (TW); Kwei-Luen Hsu, Hsinchu (TW); Chang-Mau Sheng, Taipei (TW); Ching-Jun Liou, Longtan Township, Taoyuan County (TW); Te-Sheng Liang, Taipei (TW)

(73) Assignee: Atomic Energy Council-Institute of Nuclear Energy Research, Taoyuan County (TW)

( * ) Notice: Subject to any disclaimer, the term of this patent is extended or adjusted under 35 U.S.C. 154(b) by 212 days.

(21) Appl. No.: 12/354,815

(22) Filed: Jan. 16, 2009

(65) Prior Publication Data
US 2010/0183508 A1  Jul. 22, 2010

(51) Int. Cl.
*A61K 49/00* (2006.01)

(52) U.S. Cl. .......... 424/9.1; 424/1.11; 424/1.65; 534/14
(58) Field of Classification Search ................ 424/1.11, 424/1.65, 1.73, 9.1, 9.3, 9.4, 9.5, 9.6, 9.7, 424/9.8; 534/7, 10–16
See application file for complete search history.

(56) References Cited

U.S. PATENT DOCUMENTS 7,067,508 B2 * 6/2006 Jeong et al. ................... 514/183
* cited by examiner

*Primary Examiner* — D L Jones
(74) *Attorney, Agent, or Firm* — Ming Chow; Sinorica, LLC

(57) ABSTRACT

A radioactive mixture and a manufacturing method thereof are disclosed. The radioactive mixture ($^{188}$Re-MN/Lipiodol mixture) is formed by chelating reaction of MN series compounds that are amine-amide-disulfide amine quadric-dentate chelate ligands with $TcO_4^-$/or $ReO_4^-$, and then dissolved in Lipiodol. Moreover, the $^{99m}Tc$/or $^{188}Re$ of the $TcO_4^-$/or $ReO_4^-$ avoids bone marrow injuries caused by free $^{90}Y$. By the feature of the Lipiodol that stays in liver tumors for a long period, the radioactive mixture is applied to treat liver cancers by injection so that injuries caused by surgical operations can be prevented. $^{188}$Re-MN/Lipiodol is used for liver cancer, breast cancer or other solid tumors treatment. Re-188 MN or Re-188 MN/Lipiodol can be mixed with anticancer drugs, hydrogel, liposome, micelle or other nano-particles to form the multifunctional therapeutic modality.

6 Claims, 2 Drawing Sheets

RADIOACTIVE MIXTURE AND MANUFACTURING METHOD THEREOF

BACKGROUND OF THE INVENTION

1. Field of Invention

The present invention relates to a radioactive mixture and a manufacturing method thereof, especially to a radioactive mixture and a manufacturing method thereof applied to liver cancer treatment.

2. Description of Related Art

Liver is the largest organ inside the abdominal cavity. According to sources, liver cancer is divided into two types One is called primary hepatic tumor that starts in the liver and the other is the secondary hepatic tumor that has spread from the primary site to the liver. The hepatocellular carcinoma (hepatoma) is the most common primary liver cancer.

In Americans and most of Europeans, hepatic tumor is not common. However, liver cancer is one of the most malignant tumors in Asian and African countries. According to statistics of Department of Health in 2007, cancer has become the top cause of death. Liver cancer is the first leading cause of death in men while the second in women.

Liver cancer is lack of. symptom and early syndrome. The diagnostic methods for hepatoma consist of liver ultrasound (US), computed tomography (CT) and hepatic angiography. In about 60-80% patients, the alpha-fetoprotein (AFP) in their blood increases. The AFP is a useful marker in the diagnosis of hepatocellular carcinoma. Although liver ultrasound and traditional CT detect hepatic tumors, both methods are not sensitive enough. Thus the small hepatocellular carcinoma with multiple nodules may not be detected. As to tumors smaller than 2 mm, ultrasound could not detect and the diagnosis is especially difficult in tumors with liver cirrhosis. Generally, surgery is the first choice of treatment for hepatoma. Yet the patients are often uncomfortable after surgery and the recovery period after the operation varies from patient to patient.

Lipiodol is an iodized fatty acid extracted from Poppy-seed oil. The glycerol therein is esterified by ethanol to get an iodized contrast agent that is often applied to lymph and bile duct X-ray imaging in clinical. Lipiodol can stay quite a long time inside the liver tumors. Due to a large amount of iodine in its structure, $^{131}$I-Lipidol (iodine-131-labeled lipidol) agent is get once the iodine is replace by radioactive $^{131}$I and the agent is used for radiation therapy of liver cancers. In European, $^{131}$I-Lipidol is available for liver cancer therapy. Yet the half-life of iodine-131 is as long as 13 days and emits high energy gamma rays (364 keV) while its Beta ray energy is not high. Thus this is not an ideal therapeutic nuclide. Moreover, Professor Takayasu, National Cancer Centre, Tokyo, Japan, recommends $^{90}$Y-Lipiodol that emits pure beta particles to treat liver cancers. But the half-life of the isotope $^{90}$Y is 64.1 hours. Although a lot of studies show that the nuclide feature of $^{90}$Y emitting pure beta particles ($\beta$=2.2 MeV) is much better than that of $^{131}$I, however free $^{90}$Y causes severe bone marrow damage.

Thus there is a need to provide a radioactive mixture and a manufacturing method for liver cancer treatment that not only treat liver tumors but also prevent bone marrow injuries caused by free $^{90}$Y.

SUMMARY OF THE INVENTION

Therefore it is a primary object of the present invention to provide a radioactive mixture and a manufacturing method. The radioactive mixture is radioactive $^{188}$Re-MN/Lipiodol dissolved in Lipiodol.

It is another object of the present invention to provide a radioactive mixture and a manufacturing method that treat liver cancers and prevent bone marrow injuries caused by free $^{90}$Y.

It is a further object of the present invention to provide a radioactive mixture and a manufacturing method that stay in liver tumors for a long period by means of Lipiodol.

It is an object of the present invention to provide a radioactive mixture and a manufacturing method that achieve therapeutic effects by injection so as to prevent damages caused by surgery.

In order to achieve above objects, a radioactive mixture of the present invention includes

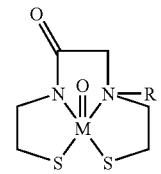

5~10% weight percent and 50~55% weight percent lipiodol; wherein R is $(CH_2)_{14}COOC_2H_5$, $(CH_2)_{13}CH_3$, or $(CH_2)_{15}CH_3$.

A manufacturing method of the radioactive mixture includes the steps of: (1) dissolve MN series compound in acetic acid and (2) add stannous chloride, glucoheptonate, $^{188}$Re-perrhenate, and Lipiodol into the solution. The solution is vibrated at a temperature controlled vibrator with temperature ranging from 70-100° C. and rotational speed 300-750 rpm for being mixed well. After centrifugation, take lower oily layer to get the radioactive mixture.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

The present invention provides a radioactive mixture and a manufacturing method thereof. The radioactive mixture includes: 5~10% weight percent

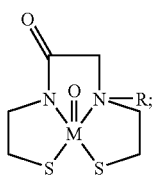

and 50~55% weight percent lipiodol; wherein R is $(CH_2)_{14}COOC_2H_5$, $(CH_2)_{13}CH_3$ or $(CH_2)_{15}CH_3$.

Chemical structure of the radioactive mixture after reaction:

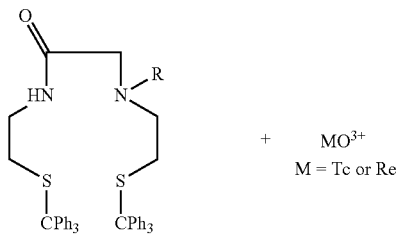

H$_3$MN-14: R = $(CH_2)_{13}CH_3$
H$_3$MN-16: R = $(CH_2)_{15}CH_3$
H$_3$MN-16ET: R = $(CH_2)_{15}COOEt$

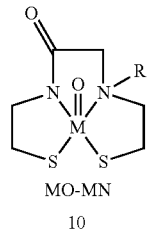

MO-MN
20

The MN series compound (drug) is an amine-amide-disulfide amine quadri-dentate chelate ligand that reacts with $TcO^{3+}$, $ReO^{3+}$, and three protons are released to form an electrically neutral compound MO-MN without protons to be released, and unable to receive external protons. The compound will not turn into anion or cation that is hydrophilic. Moreover, the long alkyl chain R increases lipid solubility of the compound. Thus the MN series compound is soluble in lipiodol.

Figure 1:
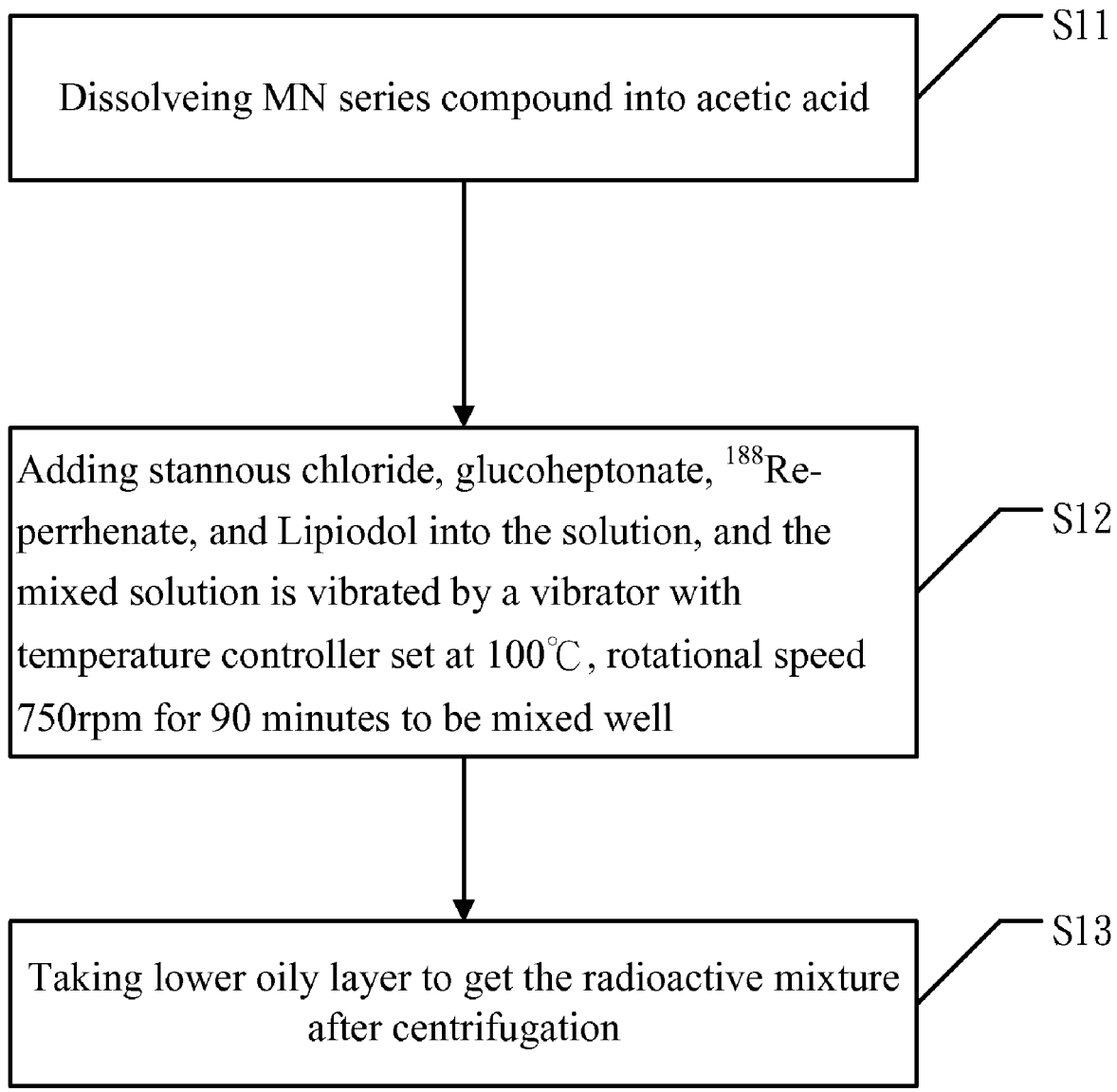
FIG. 1 is a flow chart showing steps of a manufacturing method of a radioactive mixture according to the present invention.
Figure 2A:
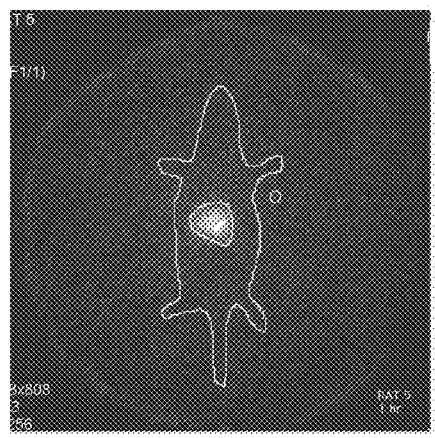
FIG. 2A is an image showing radioactivity distribution 1 hr after injection radioactive mixture into the hepatic artery.
Figure 2B:
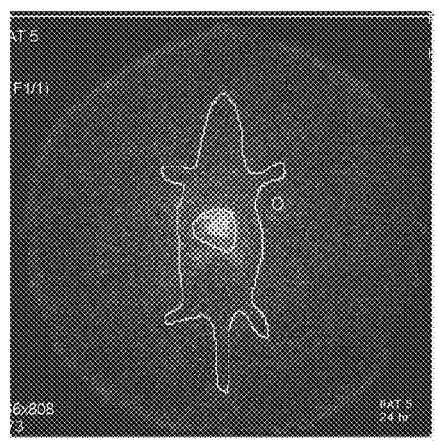
FIG. 2B is an image showing radioactivity distribution 24 hours after injection radioactive mixture into the hepatic artery.
Figure 2C:
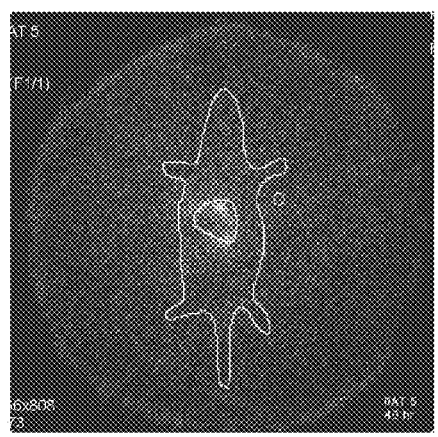
FIG. 2C is an image showing radioactivity distribution 48 hours after injection radioactive mixture into the hepatic artery.

A manufacturing method of the radioactive mixture includes the following steps, as shown in FIG. 1:

Step S11: dissolve MN series compound into acetic acid;
Step S12: then add stannous chloride, glucoheptonate, $^{188}$Re-perrhenate, and Lipiodol into the solution, and the mixed solution is vibrated by a vibrator with temperature controller set at 30-100° C., rotational speed 300-750 rpm for 30-90 minutes to be mixed well; and
Step S13: after centrifugation, take lower oily layer to get the radioactive mixture.
wherein in the step S11, the MN series compound includes: H$_3$MN-14 (N-[2-((triphenylmethyl)thio)ethyl]3-aza-3-[2-((triphenylmethyl)thio)ethyl]hepata-decane)), H$_3$MN-16(N-[2-((triphenylmethyl)thio)ethyl]3-aza-3-[2-((tri-phenylmethyl)thio)ethyl]nonadecanamide) or H$_3$MN-16ET(N-[2-((triphenyl-methyl)thio)ethyl]3-aza-18-ethyloxycarbonyl-3-[2-((tri-phenylmethyl)thio)-ethyl]octadecanamide). Because the complex formed by MN series N2S2 quadri-dentate chelate ligand with long alkyl chain and rhenium/technetium is stable and soluble in Lipiodol, the MN series compound is ideal to be applied to studies related to radioactive therapies for hepatic cancers.

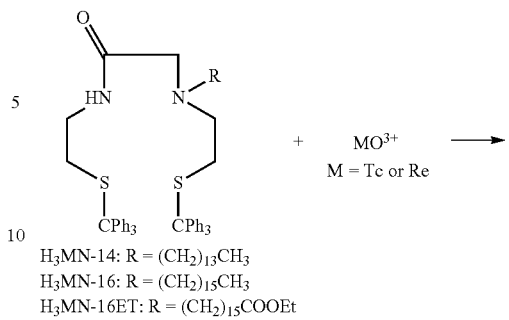

H$_3$MN-14: R = $(CH_2)_{13}CH_3$
H$_3$MN-16: R = $(CH_2)_{15}CH_3$
H$_3$MN-16ET: R = $(CH_2)_{15}COOEt$

MO-MN
10

The $^{188}$Re-perrhenate solution is prepared by a $^{188}$W/$^{188}$Re generator added with 0.9% sodium chloride solution.

Embodiment

Preparation of the radioactive mixture ($^{188}$Re-MN/Lipiodol) for liver cancer. Synthesis of $^{188}$Re-MN: Firstly, dissolve H$_3$MN-16ET compound into acetic acid, then add stannous chloride, glucohepatonate, $^{188}$Re-perrhenate solution and Lipiodol into the solution. The solution is vibrated by a vibrator with temperature controller set at 70-100° C. and 300-750 rpm for 30-90 minutes to be mixed well. Finally, the reaction bottle is centrifuged. After that, take lower oily layer to get the radioactive mixture for liver cancer treatment.

Radiochemical Analysis

The radio-chemical purity of the $^{188}$Re-MN/Lipiodol is detected by thin layer chromatography (TLC). Silica-Gel is used as the stationary phase while ethyl acetate and normal saline are as mobile phase. When the normal Saline is used as mobile phase, $^{188}$Re-MN-16ET/Lipiodol stops at the position of Rf=0. When the mobile phase is ethylacetate, $^{188}$Re-MN-16ET/Lipiodol stops at the position of Rf=0.4-0.7.

The test result shows that the extracted and purified final product—$^{188}$Re-MN-16ET/Lipiodol, its radio-chemical purity is over 95% and is stable for 24 hours.

Biodistribution of $^{188}$Re-MN-16ET/Lipiodol

Data related to in vivo tissue distribution of $^{188}$Re-MN-16ET/Lipiodol comes from 15 male rats with liver cancer. The rats are killed respectively in groups of 5 rats at 1, 24, 48 hours after injection 7.4 MBq/0.1 ml of $^{188}$Re-MN-16ET/Lipiodol into liver arteries. Taking out the following organs (tumor, normal liver, lung, kidney, spleen, testis, muscle, bone and blood) carefully and then weight them. A gamma counter is used to measure radioactivity of the tissues and calculates the tissue concentration expressed as percent injected dose per gram of organs (% inj. dose/g, % ID/g).

Following the intra-artery injection, the lipiodol solution of $^{188}$Re-MN-16ET showed high tumor-uptake in SPECT images of hepatoma-bearing rats taken at 1, 24 and 48 hours post-injection (FIG. 1). Most of the radioactivity was concentrated in the liver and hepatoma area, while little activity could be found in the lungs or other organs. A similar phenomenon was also found in the biodistribution data of $^{188}$Re- MN-16ET/Lipiodol as shown in FIG. 3. The uptakes of tumors were 11.55±1.44, 13.16±1.46 and 10.67±0.95% ID/g at 1, 24 and 48 hours post-injection, respectively (Table 1). The level of radioactivity in normal liver tissue was high, but was significantly lower than that of the tumors, while the liver, lung and spleen were found to have some radioactivity. The concentration in other organs was extremely low.

TABLE 1

Tissue concentration (% ID/g) of $^{188}$Re-MN-16ET/Lipiodol in rat organs, tissues and body fluid after being injected through hepatic arteries:

| ORGANS | TIME | | |
|---|---|---|---|
| | 1 Hr | 24 Hr | 48 Hr |
| BLOOD | 0.27 ± 0.16 | 0.13 ± 0.07 | 0.08 ± 0.05 |
| TUMOR | 11.55 ± 1.44 | 13.16 ± 1.46 | 10.67 ± 0.95 |
| LIVER | 6.96 ± 0.19 | 5.11 ± 0.28 | 3.26 ± 0.27 |
| LUNG | 0.60 ± 0.56 | 2.11 ± 0.67 | 1.12 ± 0.36 |
| SPLEEN | 0.31 ± 0.23 | 1.38 ± 0.71 | 0.81 ± 0.92 |
| MUSCLE | 0.05 ± 0.02 | 0.14 ± 0.20 | 0.04 ± 0.05 |
| BONE | 0.06 ± 0.01 | 0.18 ± 0.30 | 0.02 ± 0.02 |
| TESTIS | 0.04 ± 0.01 | 0.06 ± 0.06 | 0.01 ± 0.00 |
| INTESTINE | 0.38 ± 0.41 | 0.35 ± 0.18 | 0.10 ± 0.08 |
| KIDNEY | 0.31 ± 0.16 | 0.42 ± 0.16 | 0.10 ± 0.03 |
| URINE | 0.00 ± 0.00 | 0.41 ± 0.34 | 0.68 ± 0.61 |

In summary, the present invention has the following features:
1. A radioactive mixture of the present invention is a whole new mixture.
2. The present invention prevents bone marrow injuries caused by free $^{90}$Y.
3. By the feature of the Lipiodol that stays in liver tumors for a long period, the radioactive mixture offers new hope for liver cancer treatment.
4. The radioactive mixture is applied to treat tumors by injection so that injuries caused by surgical operations can be avoided.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:
1. A radioactive mixture for the treatment and diagnosis of liver cancer comprising:
5-10% weight percent

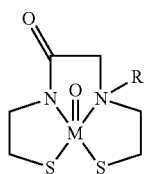

and 50-55% weight percent Lipiodol, wherein M is $^{99m}$Tc or $^{188}$Re, and R is $(CH_2)_{14}COOC_2H_5$.

2. A method of manufacturing a radioactive mixture for the treatment and diagnosis of liver cancer comprising the steps of: (i) dissolving

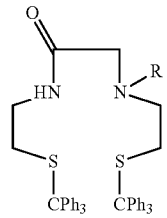

wherein R is $(CH_2)_{14}COOC_2H_5$ in acetic acid to form an acetic solution;
(ii) adding stannous chloride, glucoheptonate, $^{188}$Re-perrhenate or $^{99m}$Tc, and Lipiodol into the acetic solution to form a mixed solution;
(iii) centrifuging the mixed solution; and
(iv) removing lower oily layer which is the radioactive mixture comprising

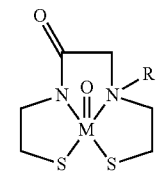

and Lipiodol, wherein M is $^{99m}$Tc or $^{188}$Re and R is $(CH_2)_{14}COOC_2H_5$.

3. The method of claim 2 wherein step (iii) comprises vibrating the mixed solution in a vibrator with a temperature controller set at 70-100° C. and a rotation speed of 300-750 rpm for 30-90 minutes.

4. A method of treating liver cancer comprising intra-tumoral injection or transarterial embolization of the radioactive mixture of claim 1 into a subject and monitoring radioactivity in organs of said subject.

5. A method of diagnosing liver cancer comprising injecting the radioactive mixture of claim 1 into arteries of the liver of a subject and imaging said subject.

6. A radioactive compound of Formula

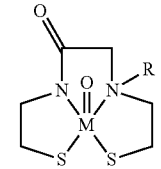

wherein M is $^{99m}$Tc or $^{188}$Re and R is $(CH_2)_{14}COOC_2H_5$.

\* \* \* \* \*